(12) United States Patent
Nakamura et al.

(10) Patent No.: US 6,554,772 B2
(45) Date of Patent: Apr. 29, 2003

(54) ULTRASONIC DIAGNOSIS DEVICE

(75) Inventors: Takahiko Nakamura, Chiba (JP); Masataka Shinogi, Chiba (JP); Keisuke Tsubata, Chiba (JP)

(73) Assignee: Seiko Instruments Inc. (JP)

( * ) Notice: Subject to any disclaimer, the term of this patent is extended or adjusted under 35 U.S.C. 154(b) by 0 days.

(21) Appl. No.: 10/027,063

(22) Filed: Dec. 26, 2001

(65) Prior Publication Data

US 2002/0128556 A1 Sep. 12, 2002

(30) Foreign Application Priority Data

Jan. 22, 2001 (JP) ......................... 2001-012878

(51) Int. Cl.$^7$ ................................ A61B 8/14
(52) U.S. Cl. .................................... 600/459
(58) Field of Search ................. 600/437, 443, 600/459, 460, 455, 503, 445, 444, 446

(56) References Cited

U.S. PATENT DOCUMENTS 6,036,653 A * 3/2000 Baba et al. ............... 600/500
6,334,850 B1 * 1/2002 Amano et al. ............ 600/500
6,447,456 B1 * 9/2002 Tsubata .................... 600/455

* cited by examiner

Primary Examiner—Francis J. Jaworski
Assistant Examiner—Maulin Patel
(74) Attorney, Agent, or Firm—Adams & Wilks

(57) ABSTRACT

To provide an ultrasonic diagnosis device which can be simply manufactured and can detect an ultrasonic wave with excellent sensitivity and accuracy. An ultrasonic diagnosis device in which a transmitting piezoelectric element and a receiving piezoelectric element are supported on a substrate supported parallel to a radial artery by support means such that their widths a, c are respectively 0.38–1.1 mm and a gap b between them is 0.05–4.0 mm, an ultrasonic wave is transmitted from the transmitting piezoelectric element, a reflected wave from the radial artery is received by the receiving piezoelectric element, and a pulse wave is detected on the basis of a detection result of the reflected wave.

2 Claims, 10 Drawing Sheets

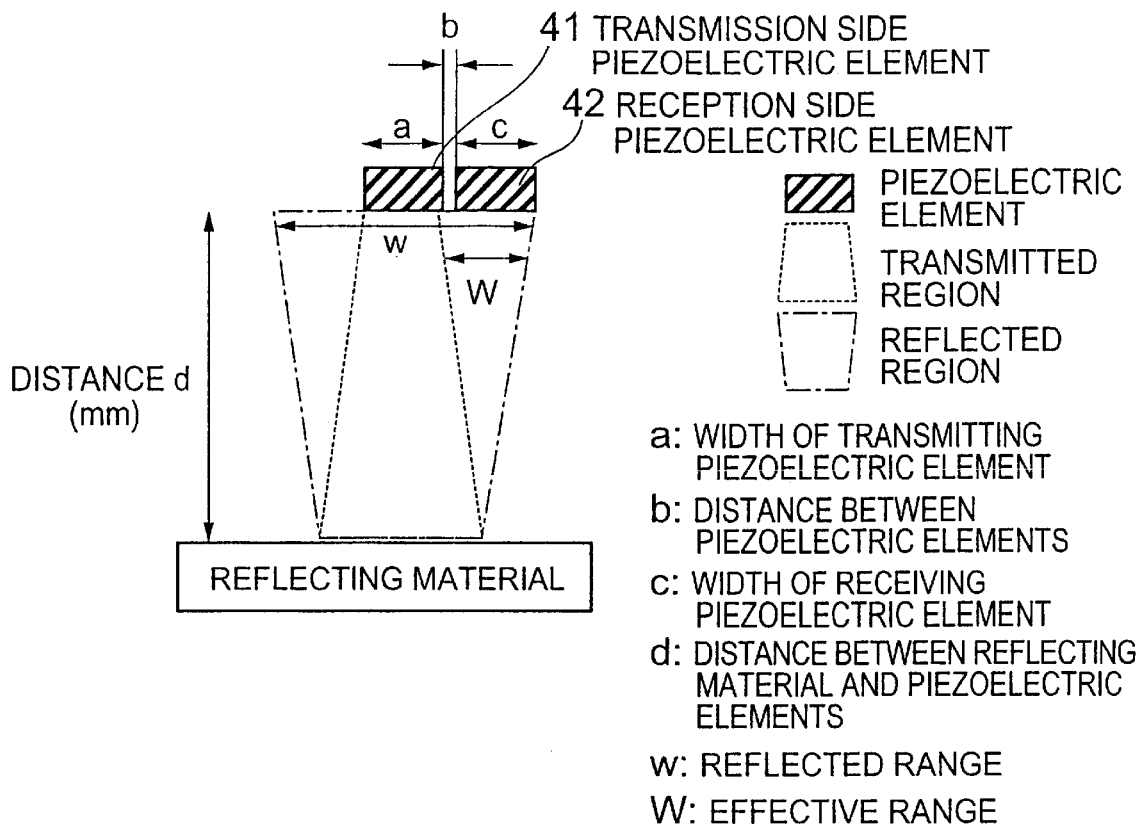

FIG.5

$$D_w(\theta) = \frac{\sin(x_\theta)}{x_\theta}$$

$$x_\theta = \frac{\pi \cdot a}{\lambda} \sin \theta$$

$D(\theta)$: DIRECTIONAL FUNCTION
$\theta$: DIRECTIVITY ANGLE
$\lambda$: WAVELENGTH
a: WIDTH OF TRANSMITTING PIEZOELECTRIC ELEMENT
b: DISTANCE BETWEEN PIEZOELECTRIC ELEMENT
c: WIDTH OF RECEIVING PIEZOELECTRIC ELEMENT
d: DISTANCE BETWEEN REFLECTING MATERIAL AND PIEZOELECTRIC ELEMENTS
w: REFLECTED RANGE
W: EFFECTIVE RANGE

FIG.6

ULTRASONIC DIAGNOSIS DEVICE

BACKGROUND OF THE INVENTION

1. Field of the Invention

The present invention relates to an ultrasonic diagnosis device, such as a pulse wave detection device and an ultrasonic image diagnosis device, for obtaining an information of a diagnostic region on the basis of, by transmitting an ultrasonic wave to the diagnostic region, its reflected wave and, in detail, it is concerned in an ultrasonic diagnosis device which can be simply manufactured and can detect the ultrasonic wave with excellent sensitivity and accuracy.

2. Description of the Prior Art

Hitherto, there has been well known the ultrasonic diagnosis device, such as the pulse wave detection device and the ultrasonic image diagnosis device, for obtaining the information of the diagnostic region on the basis of, by transmitting the ultrasonic wave to the diagnostic region, its reflected wave.

FIG. 17 is a drawing showing one example of a sensor section of such an ultrasonic diagnosis device of the prior art. As shown in FIG. 17, this ultrasonic diagnosis device has, in its sensor section 100, a transmitting piezoelectric element 141 for transmitting the ultrasonic wave and a receiving piezoelectric element 142 for receiving the ultrasonic wave. And, these piezoelectric elements 141, 142 are fixed to a support body 146 so as to be disposed obliquely to a measuring region. These piezoelectric elements 141, 142 are fixed to the support body 146 by disposing them in predetermined positions of the support body 146 and thereafter pouring and curing a resin.

In the ultrasonic diagnosis device of the prior art mentioned above, by the fact that the two piezoelectric elements 141, 142 are disposed obliquely to the support body 146, the reflected wave is received in its wide range by the receiving piezoelectric element 142 to thereby improve a measuring sensitivity.

However, such an ultrasonic diagnosis device of the prior art requires to fix the piezoelectric elements by the resin and work the support body obliquely, and thus takes much time in its manufacture. Besides, in case of fixing by the resin, there is a possibility that disposing positions and disposing angles of the piezoelectric elements are deviated when pouring the resin, so that there is a possibility that the piezoelectric elements cannot be disposed with a high positional accuracy and thus it is difficult to obtain improvements in the measuring sensitivity and accuracy.

The present invention has been made in order to solve such a problem as mentioned above, and its object is to provide an ultrasonic diagnosis device which can be simply manufactured and can obtain high sensitivity and measuring accuracy.

SUMMARY OF THE INVENTION

The present invention achieves the object mentioned above by providing an ultrasonic diagnosis device (1st constitution) comprising a transmitting piezoelectric element for transmitting an ultrasonic wave to a diagnosis region, a receiving piezoelectric element for receiving a reflected wave of the ultrasonic wave from the diagnosis region, support means for supporting the transmitting piezoelectric element and the receiving piezoelectric element, and information obtainment means for obtaining an information of the diagnosis region on the basis of the reflected wave received by the receiving piezoelectric element, in which the support means has a planar face disposed approximately parallel to the diagnosis region, and the transmitting piezoelectric element and the receiving piezoelectric element are disposed on the planar face of the support means by a relation satisfying the following conditions 1 or conditions 2 in case where it is supposed that a width of the transmitting piezoelectric element is a, a distance between the transmitting piezoelectric element and the receiving piezoelectric element b, a width of the receiving piezoelectric element c, a distance up to a measuring region d and a directivity angle $\theta$:

$c/(2d \tan \theta) \geq 0.1$ and $0 < b$ 23 $2d \tan \theta - c$   conditions 1

$(2d \tan \theta - b)/(2d \tan \theta) 24$ $0.1$ and $2d \tan \theta - c < b < 2d \tan \theta$.   conditions 2

The present invention achieves the object mentioned above by providing an ultrasonic diagnosis device comprising a transmitting piezoelectric element for transmitting an ultrasonic wave to a diagnosis region, a receiving piezoelectric element for receiving a reflected wave of the ultrasonic wave from the diagnosis region, support means for supporting the transmitting piezoelectric element and the receiving piezoelectric element, and information obtainment means for obtaining an information of the diagnosis region on the basis of the reflected wave received by the receiving piezoelectric element, which in that the support means has a planar face disposed parallel to the diagnosis region, and the transmitting piezoelectric element and the receiving piezoelectric element are disposed on the planar face of the support means such that their widths are respectively 0.38 to 1.1 mm, and a gap between them is 0.05 to 4.0 mm.

BRIEF DESCRIPTION OF THE SEVERAL VIEWS OF THE DRAWINGS

A preferred form of the present invention is illustrated in the accompanying drawings in which:

FIG. 5 is an explanatory view showing transmitting and receiving states of an ultrasonic wave by the pulse wave detection device of FIG. 1;

FIG. 6 is a view showing expressions representing the transmitting and receiving states of the ultrasonic wave by the pulse wave detection device of FIG. 1;

DETAILED DESCRIPTION OF THE PREFERRED EMBODIMENTS

Figure 1:
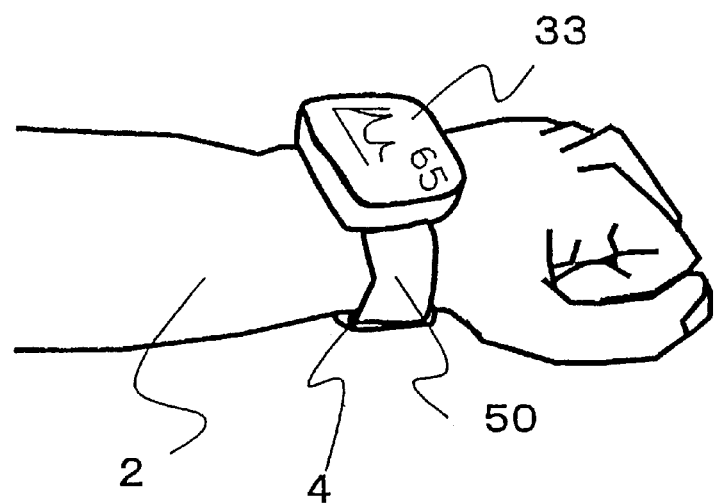
FIG. 1 is a perspective view showing a pulse wave detection device as one embodiment of an ultrasonic diagnosis device of the present invention in a state that it has been worn on a subject.

Hereunder, it is detailedly explained about embodiments of the present invention by referring to the drawings.

First, it is detailedly explained about a 1st embodiment of the present invention by referring to FIG. 1 to FIG. 7.

Figure 2:
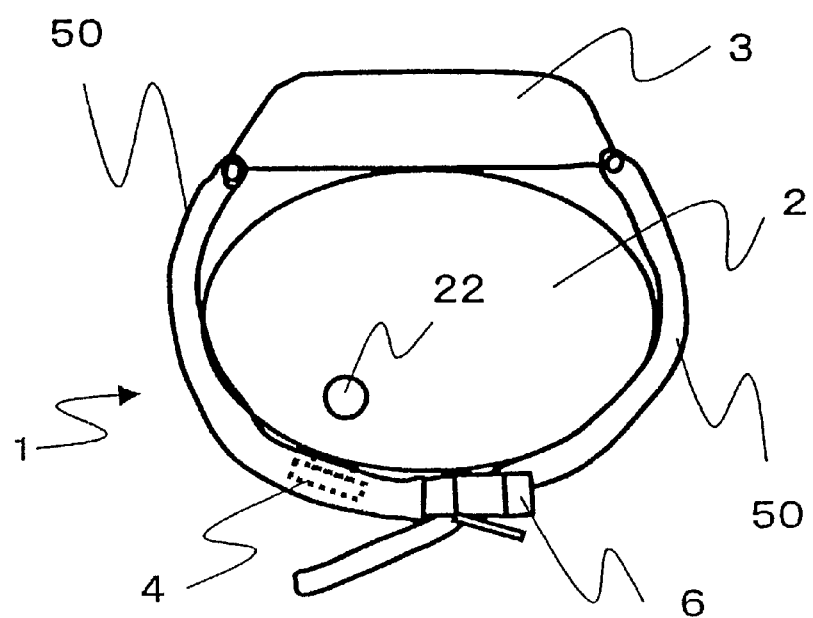
FIG. 2 is a side view seen from an arm's root side of the subject in the state that the pulse detection device of FIG. 1 has been worn on the subject.

FIG. 1 is a perspective view showing a pulse wave detection device as the 1st embodiment of an ultrasonic diagnosis device of the present invention in a state that it has been worn on a subject. FIG. 2 is a side view in which the pulse wave detection device of FIG. 1 is seen from an arm's root side of the subject toward a finger side in the state that it has been worn on the subject.

As shown in FIG. 1 and FIG. 2, the ultrasonic diagnosis device (pulse wave detection device) 1 of this embodiment has a sensor section 4 which is butted against a body surface of the subject, transmits an ultrasonic wave from the body surface of the subject to a radial artery of the subject as a diagnostic region and receives a reflected wave, and a belt 50 which is wound around a wrist of the subject to be fixed by a fastener 6 and fixedly supports the sensor section 4 to the subject. The sensor section 4 is supported on an inner periphery face (face of a subject side) of the belt 50 in a wearing state.

In a midway of the belt 50, there is disposed through metal fittings a processing section 3 as information obtainment means for obtaining a pulse wave as an information of the radial artery on the basis of the reflected wave received by the sensor section 4. The processing section 3 has a display part 33 in an outer periphery face side in the wearing state of the belt 50.

And, it is adapted such that, if the processing section 3 is attached to a left (or right) wrist 2 of a wearer on his/her hand's back side, the sensor section 4 is fixed while being positioned approximately on a radial artery 22 of the wearer.

Figure 3:
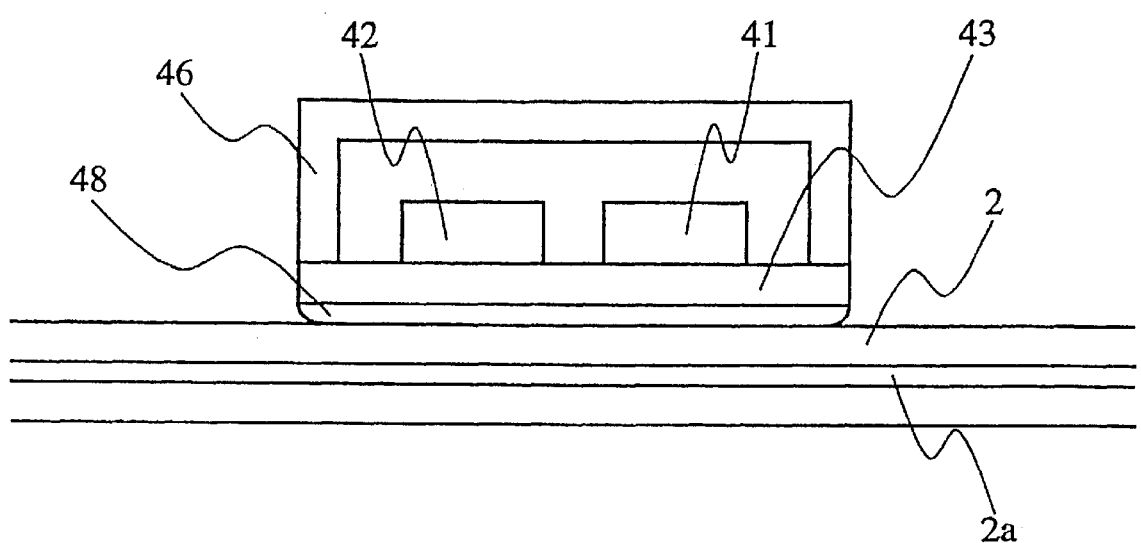
FIG. 3 is a main portion enlarged sectional view in which a sensor section of the pulse wave detection device of FIG. 1 has been cut in a longitudinal direction of a belt.

FIG. 3 is a main portion enlarged sectional view in which the sensor section 4 has been cut in a longitudinal direction of the belt 50.

As shown in FIG. 3, the sensor section 4 has a substrate 43 having electrodes, a transmitting piezoelectric element 41 for transmitting the ultrasonic wave to the radial artery, and a receiving piezoelectric element 42 for receiving the reflected wave from the radial artery. These piezoelectric elements (the transmitting piezoelectric element 41 and the receiving piezoelectric element 42) are fixedly supported on the substrate 43.

The transmitting piezoelectric element 41 and the receiving piezoelectric element 42 are PZTs whose widths (lengths in a direction along which the transmitting piezoelectric element 41 and the receiving piezoelectric element 42 are arrayed) a, c are respectively 0.38 to 1.1 mm, in which a gap b between them is 0.05 to 4.0 mm, and whose thicknesses are 0.2 mm (resonance frequency 9.6 MHz).

On both faces in a depth direction of each of the transmitting piezoelectric element 41 and the receiving piezoelectric element 42, there are formed electrodes not shown in the drawing. And, these electrodes are respectively connected to signal wires (not shown in the drawing) embedded in the belt 50 through the substrate 43.

The substrate 43 has a planar form of 10×11 mm and 0.5 mm in thickness. This substrate 43 is formed of a glass or the like. On a face (one face), of this substrate 43, becoming a wearer side when wearing, the piezoelectric elements 41, 42 are fixed and supported. Incidentally, in case where the substrate 43 is formed by epoxy resin and acryl group resin, etc., it is possible to cause this substrate 43 to function as an acoustic matching layer by setting such that its acoustic impedance Zm becomes a value between an acoustic impedance Z1 of an organism and an acoustic impedance Zc of the piezoelectric elements 41, 42. The acoustic impedance means a value representing an easiness in propagation of a sound wave, and this value changes by Young's modulus and density of a material. An ideal acoustic impedance Zm of the acoustic matching layer can be represented by the following expression (1).

$$Zm = (Zc \times Z1)^{1/2} \quad (1)$$

And, if the following mathematical expressions (2) and (3) which have been publicly known are substituted for the mathematical expression (1), a value of Zm is found like a mathematical expression (4).

$$Z1 \times 1.5 \times 10^6 \; (N \cdot sec/cubic \; meter) \; (fat) \quad (2)$$

$$Zc \; (when \; PZTs \; are \; used) = 30 \times 10^6 \; (N \cdot sec/cubic \; meter) \quad (3)$$

$$Zm \approx 6.7 \times 10^6 \; (N \cdot sec/cubic \; meter) \quad (4)$$

The transmitting piezoelectric element 41 and the receiving piezoelectric element 42 are fixed to the aforesaid one face of the substrate 43 such that the gap between them becomes 0.05 to 4.0 mm.

Besides, in this embodiment, a directivity angle of the ultra wave transmitted from the transmitting piezoelectric element (angle from a direction perpendicular to a surface of the transmitting piezoelectric element 41) is set so as to satisfy the followings.

$$c/(2d \tan \theta) \geq 0.1 \text{ and } 0 < b \leq 2d \tan \theta - c \quad (5)$$

Incidentally, b is the distance between the transmitting piezoelectric element 41 and the receiving piezoelectric element 42, c the width of the receiving piezoelectric element, d the distance up to a measuring region, and θ the directivity angle.

Besides, to the substrate 43 there is fixed a support body 46 having an approximately U-shaped form in section at a face (the aforesaid one face) of a side, on which the piezoelectric elements 41, 42 are fixed, so as to accommodate therein the piezoelectric elements 41, 42. This support body 46 is fixed to the belt 50 at an outer face in a side opposite to the substrate 43. By this, the substrate 43 is reinforced by the support body 46, and the piezoelectricelements 41, 42 are protected. Besides, a space inside the support body 46 functions as an ultrasonic attenuation section and, since the ultrasonic wave transmitted from the piezoelectric elements 41, 42 to a belt 50 side and the ultrasonic wave entering from an outside into the belt are attenuated, a noise received by the receiving piezoelectric element 42 is reduced, so that it becomes possible to detect the pulse wave information with a high sensitivity.

Further, the substrate 43 has an acoustic matching layer 48 at a face (the other face) becoming the wearer side when wearing, which is a side opposite to the aforesaid one face. By this, the acoustic matching layer 48 is disposed between the piezoelectric elements 41, 42 and the organism. This acoustic matching layer 48 is formed by epoxy resin and acryl group resin, etc., and its acoustic impedance Zm is set to a value between the acoustic impedance Z1 of the organism and the acoustic impedance Zc of the piezoelectric elements 41, 42. The acoustic impedance means the value representing the easiness in propagation of the sound wave, and this value changes by Young's modulus and density of the material. The ideal acoustic impedance Zm of the acoustic matching layer can be represented by the following expression (6).

$$Zm = (Zc \times Z1)^{\frac{1}{2}} \quad (6)$$

And, if the following expressions (7) and (8) which have been publicly known are substituted for the expression (6), a value of Zm is found like a mathematical expression (9).

$$Z1 = 1.5 \times 10^6 \ (N \cdot \text{sec/cubic meter}) \ (\text{fat}) \quad (7)$$

$$i \ Zc \ (\text{when PZTs are used}) = 30 \times 10^6 \ (N \cdot \text{sec/cubic meter}) \quad (8)$$

$$Zm \approx 6.7 \times 10^6 \ (N \cdot \text{sec/cubic meter}) \quad (9)$$

On both faces in the depth direction of each of the transmitting piezoelectric element 41 and the receiving piezoelectric element 42, there are formed electrodes not shown in the drawing. And, these electrodes are respectively connected to signal wires (not shown in the drawing) embedded in the belt 50 through the substrate 43.

And, the transmitting piezoelectric element 41 receives a drive signal through the substrate 43 and the signal wires embedded in the belt 50, and transmits the ultrasonic wave of 9.6 MHz toward the artery. Incidentally, in this embodiment, the transmitting piezoelectric element 41 is adapted so as to be excited at 9.6 MHz. However, in case where the pulse wave detection device 1 is disposed in a watch, by causing the transmission frequency to be 32 KHz common to that of the watch, it is possible to use in common a transmitter of the watch to thereby suppress the number of parts of the pulse wave detection device 1, thereby inexpensively suppressing a manufacturing cost.

Figure 4:
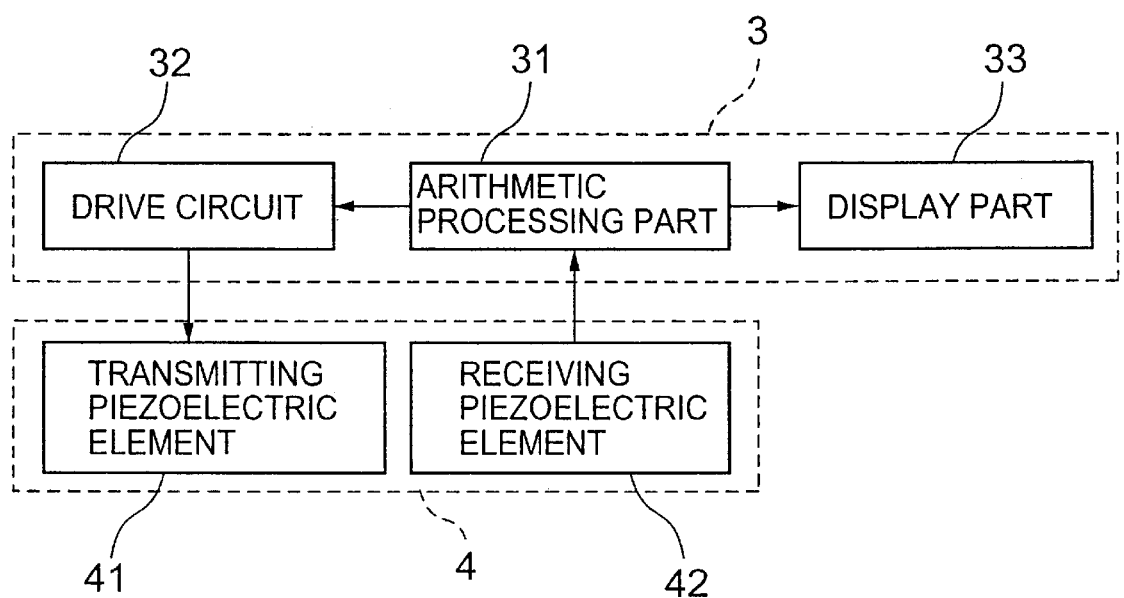
FIG. 4 is a block diagram showing a constitution of the pulse wave detection device of FIG. 1.

FIG. 4 is a block diagram showing a constitution of the pulse wave detection device 1 of FIG. 1.

As shown in FIG. 4, the processing section 3 has a drive circuit 32 for transmitting the drive signal driving the transmitting piezoelectric element 41, an arithmetic processing part 31 for obtaining a pulse wave waveform and a pulse number by processing a signal basing on the ultrasonic wave received by the receiving piezoelectric element 42, and the display part 33 for displaying the pulse wave waveform and the pulse number obtained by the arithmetic processing part 31.

The arithmetic processing part 31 carries out various processings concerning the detection of the pulse by executing a processing program stored in a storage region (not shown in the drawing) provided inside. Concretely, it outputs the drive signal from the drive circuit 32 to the transmitting piezoelectric element 41 of the sensor section 4. Besides, it detects the pulse wave and forms a pulse wave signal by comparing a frequency of the ultrasonic wave transmitted from the transmitting piezoelectric element 41 with a frequency of the ultrasonic wave which has been received by the receiving piezoelectric element 42 and changed by Doppler effect of a bloodstream. If theultrasonic wave is transmitted to the radial artery or an ulnar artery, the Doppler effect is generated by the bloodstream, so that the reflected wave is changed in its frequency with respect to the transmitted ultrasonicwave. And, by detecting this change, a change in blood velocity is detected. Since the change in blood velocity is synchronized with the pulse, it is possible to detect an information concerning the pulse. Besides, a time interval between peaks of the pulse signal is measured by a predetermined number of times (for example, three times, five times, seven times, ten times, etc.), and a pulse wave number V per one minute (= pulse rate, and heart rate) is found in compliance with the following expression (10) from a mean time T of a measuring time in each time.

$$V = 60/T \quad (10)$$

Pulse wave detection results such as the pulse wave signal and the pulse wave number V are outputted to a display unit.

Incidentally, not limited to the case where the pulse number is found from the mean time T between the pulse waves, it may be adapted such that, for example, a pulse wave number w existing within a predetermined time t (e.g., 10 seconds) is detected, and the pulse wave number V per one minute is found by the following mathematical expression (11).

$$V = w \times (60/t) \quad (11)$$

The drive circuit 32 has a transmission source by an oscillator such as quartz, generates an alternating current of a frequency complying with a natural vibration number of the transmission source, and divides that frequency into one over several. And, a specified drive signal is transmitted to the transmitting piezoelectric element 41 through the signal wire in compliance with a directive of the arithmetic processing part 31, thereby driving the transmitting piezoelectric element 41. By this, the ultrasonic wave is transmitted from the transmitting piezoelectric element 41 toward the body surface of the wearer.

The display part 33 is composed of a liquid crystal display unit and the like, and image-displays the pulse wave detection results, such as the pulse wave waveform and the pulse rate, inputted from the arithmetic processing part 31. This display part 33 may be adapted so as to display by electric light the pulse wave number to a panel.

FIG. 5 is an explanatory view showing transmitting and receiving states of the ultrasonic wave by the pulse wave detection device of FIG. 1, and FIG. 6 is an explanatory view showing expressions representing the transmitting state of FIG. 5.

The pulse wave detection device 1 having such a constitution as mentioned above is positioned on the body surface such that the sensor section 4 exists approximately above the radial artery 22 when measuring the pulse wave, and it is fixed around the wrist 2 of the subject by tightening the belt 50.

In this state, if an electric source of the pulse wave detection device 1 is turned on, the drive circuit 32 drives the transmitting piezoelectric element 41, and the ultrasonic wave whose frequency is 9.6 MHz is transmitted from the transmitting piezoelectric element 41 toward the radial artery 22. On this occasion, the ultrasonic wave from the transmitting piezoelectric element 41 is transmitted at the directivity angle $=\theta$ as shown in FIG. 5.

The ultrasonic wave transmitted toward the radial artery 22 is reflected by the bloodstream in the radial artery, 22. The ultrasonic wave is attenuated and amplitude-modulated by the bloodstream. A degree of this amplitude modulation is changed in compliance with a blood pressure. Accordingly, the reflected wave becomes a waveform having been amplitude-modulated in compliance with the blood pressure.

On this occasion, a directional function $Dw(\theta)$ is represented by an expression (12) shown in FIG. 6.

And, as to the ultrasonic wave transmitted from the transmitting piezoelectric element 41, one whose $$\text{directional function } Dw(\theta)=0 \tag{13}$$

, i.e., one whose $$\theta=\sin{-1} (n\lambda/a) \tag{14},$$

is the strongest, and contributes to the detection of the pulse wave or the like by the ultrasonic wave. Incidentally, a is the width of the transmitting piezoelectric element.

Accordingly, if the transmitting piezoelectric element 41 and the receiving piezoelectric element 42 are disposed such that the ultrasonic wave transmitted at such a directivity angle $\theta$ as satisfying the expression (14) is received by the receiving piezoelectric element 42, it becomes possible to detect the pulse wave with an excellent sensitivity.

Figure 7:
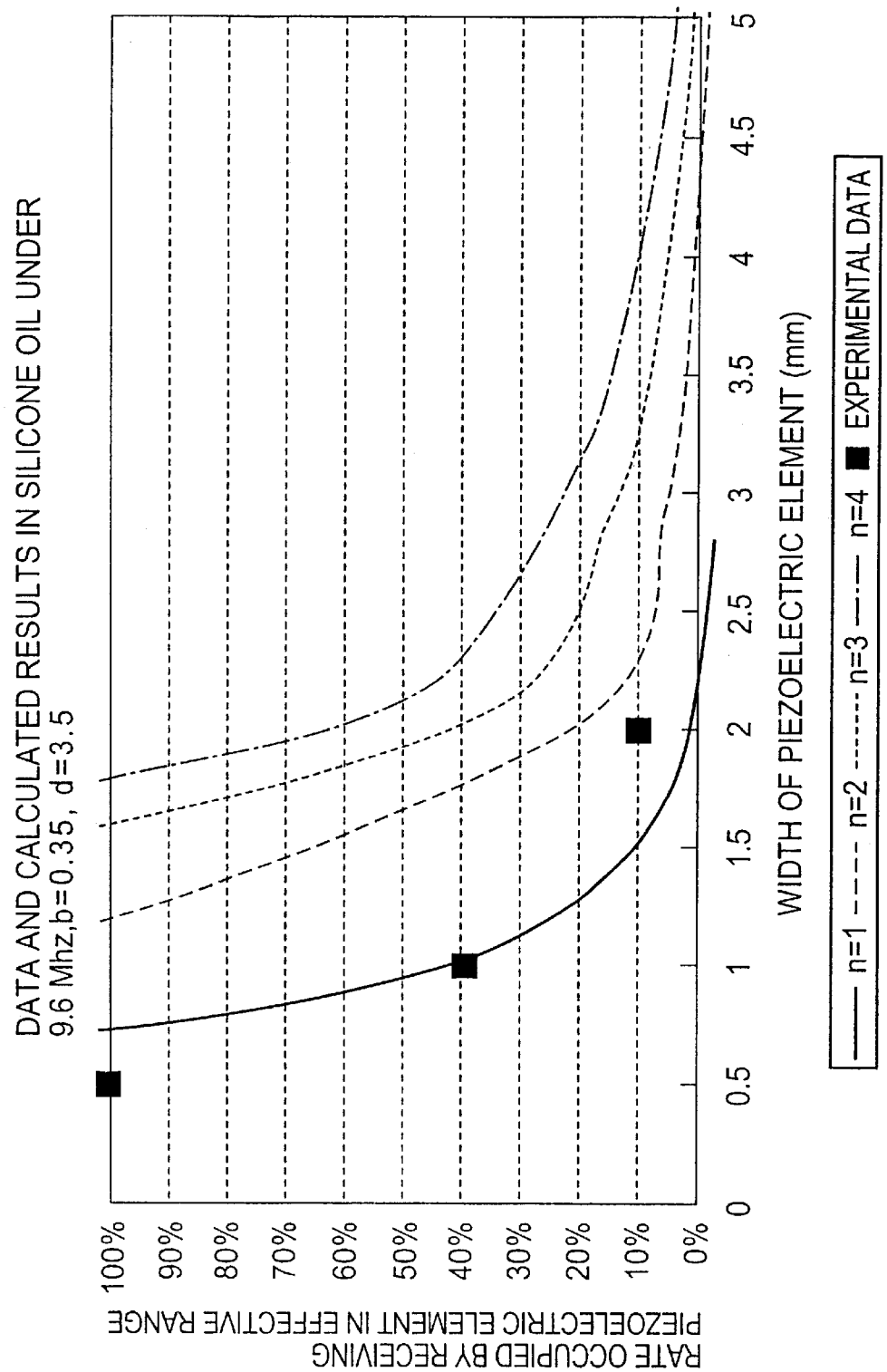
FIG. 7 is a graph in which receiving situations in a receiving piezoelectric element of the ultrasonic wave transmitted from a transmitting piezoelectric element of the pulse wave detection device of FIG. 1 are compared by experimental values and calculated values.

FIG. 7 is a graph in which receiving situations in the receiving piezoelectric element of the ultrasonic wave transmitted from the transmitting piezoelectric element are compared by experimental values and calculated values by the expression (14).

The experimental values are ones obtained by performing the experiments under the following conditions. That is, three kinds of pairs of the piezoelectric elements (the transmitting piezoelectric element and the receiving piezoelectric element) of 8 mm in length, 0.2 mm in thickness, and respectively 0.5 mm, 1 mm and 2 mm in width were prepared, each pair was fixed to a resin made substrate of 0.07 mm in thickness with a gap between the piezoelectric elements being made 0.35 mm, and the ultrasonic wave was transmitted at the drive frequency 9.6 MHz to a brass plate spaced by 3.5 mm from the transmitting piezoelectric element in silicone oil, thereby obtaining the reflected wave. And, on calculation, in case of the piezoelectric elements pair of 0.5 mm in width, since it is inferred that the whole face of the receiving piezoelectric element is in an effective range (the whole face of the receiving piezoelectric element is receiving the ultrasonic wave) and, in case of the other piezoelectric elements pairs, since it is inferred that a part is extending into the effective range, rates in which the receiving piezoelectric elements of the piezoelectric elements pairs of 1 mm and 2 mm in width exist in the effective range were computed by comparing output voltages.

The calculated values by the expression (14) are rates occupied by the receiving piezoelectric element 42 in the effective range with respect to the widths (a, c (=a)) of the piezoelectric elements in case where it is supposed that n =1, 2, 3, 4,$\lambda$=0.156 $\mu$m and d=3.5 mm.

And, in FIG. 7, the experimental values are plotted to the rates occupied by the receiving piezoelectric element 42 in the effective range with respect to the widths (a, c (in this embodiment, a=c)) of the piezoelectric elements, which is obtained by the expression (14).

As shown in FIG. 7, the calculated values in case where it is supposed that n=1 are nearest to the experimental values, so that the ultrasonic wave transmitted from the transmitting piezoelectric element 41 is appropriate as $\theta$=sin −1 ($\lambda$/a).

Accordingly, hereafter, if the transmitting piezoelectric element 41 and the receiving piezoelectric element 42 are disposed such that the ultrasonic wave transmitted at such a directivity angle $\theta$ as satisfying $$\theta=\sin{-1} (\lambda/a) \tag{15}$$

by supposing that n =1 in the expression (14) is received by the receiving piezoelectric element 42, it becomes possible to detect the pulse wave with the excellent sensitivity.

A reflected range w and an effective range W, which are shown in FIG. 5, can be represented by the following expressions.

$$w=4d \tan \theta+a \tag{16}$$

$$W=(w-a)/2 =2d \tan \theta \tag{17}$$

Besides, a range of b in which the receiving piezoelectric element 42 falls into the effective range W becomes $$0 <b \geqq 2\ d \tan \theta c \tag{18}$$

and a range of b in which the receiving piezoelectric element 42 partially enters into the effective range w becomes $$2d \tan \theta-c <b <2d \tan \theta \tag{19}.$$

And, in a state that the receiving piezoelectric element 42 is falling into the effective range W, a rate of the receiving piezoelectric element among the effective range W, i.e., a rate E detected by the receiving piezoelectric element among the reflected wave, becomes $$E =c/W =c/ (2d \tan \theta) \tag{20}$$

and, besides, in a state that the receiving piezoelectric element 42 is partially entering into the effective range W, the rate of the receiving piezoelectric element among the effective range W, i.e., the rate E detected by the receiving piezoelectric element among the reflected wave, becomes $$E =(w-b)/W=(2d \tan \theta 31\ b)/(2d \tan \theta) \tag{21}.$$

And, among the reflected wave, if 10% or more is being received in the receiving piezoelectric element, the pulse wave can be detected with the excellent sensitivity. That is, under the condition of the expression (18), E of the expression (20) is E≧0.1 or, under the condition of the expression (19), E of the expression (21) is E≧0.1.

As mentioned above, in this embodiment, it is set so as to be 0 <b≧2d tan θ−c and satisfy c/(2d tan θ)24 0.1.

In the range of W, the reflected wave is received by the receiving piezoelectric element 42. On this occasion, in this embodiment, the receiving piezoelectric element 42 falls into the effective range W and becomes a state satisfying the a fore said expression (7). And, in the state that the receiving piezoelectric element 42 is falling into the effective range W, the rate of the receiving piezoelectric element among the effective range W, i.e., the rate E detected by the receiving piezoelectric element among the reflected wave, is represented by the aforesaid expression (9), and it becomes E≧0.1. Accordingly, among the reflected wave, 10% or more is received by the receiving piezoelectric element 42.

In the receiving piezoelectric element 42, a received signal is generated on the basis of the reflected wave having been received. This received signal is transmitted from the receiving piezoelectric element 42 to the arithmetic processing part 31 of the processing section 3 through a signal wire not shown in the drawing.

In the arithmetic processing part 31, the signal having been received is detected similarly to a usual AM detection. That is, after a rectification by diode and a smoothing by condenser, a detection signal is obtained as a both-terminal voltage of load resistance. And, on the basis of this detection signal, the pulse rate is counted, and a pulse wave signal is formed.

The pulse rate counted in the arithmetic processing part 31 and the pulse wave signal are supplied to the display part 33, and the pulse rate and the pulse wave signal are displayed in the display part 33.

In this embodiment, the detection was performed using the usual AM detection, but a frequency of the reflected wave changed by the Doppler effect owing to the bloodstream may be detected. In this case, it is necessary to suitably modify the arithmetic processing part 31.

In this manner, in the pulse wave detection device 1 of this embodiment, the transmitting piezoelectric element 41 and the receiving piezoelectric element 42 are disposed onto the planar face (one face) of the substrate 43 parallel to the radial artery 2. Therefore, since it is unnecessary to obliquely dispose the piezoelectric elements 41, 42, it is unnecessary to obliquely work the substrate 43 for fixing the piezoelectric elements 41, 42 and the support body 46 to which the substrate 43 is fixed, and it is also unnecessary to manufacture the device by curing the resin. Accordingly, the manufacture is simple.

In the pulse wave detection device 1 of this embodiment, since the receiving piezoelectric element 42 receives 10% or more among the reflected wave from a radial artery 2a, it is possible to obtain high measuring sensitivity and measuring accuracy in a measurement of the pulse wave on the basis of the reflected wave.

In the pulse wave detection device 1 of this embodiment, since the transmitting piezoelectric element 41 and the receiving piezoelectric element 42 are fixed to the substrate 43 of a planar plate form, it is unnecessary to fix them by disposing them in the resin and curing the resin, so that it is possible to accurately fix the transmitting piezoelectric element 41 and the receiving piezoelectric element 42 and, also in this point, it is possible to obtain high measuring sensitivity and measuring accuracy.

Next, it is explained about a 2nd embodiment of the ultrasonic diagnosis device of the present invention. Incidentally, this 2nd embodiment is one in which the present invention has been applied also to the pulse wave detection device similarly to the aforesaid embodiment. In this 2nd embodiment, as to a member similar to the aforesaid 1st embodiment, the same reference numeral is affixed and its explanation is omitted.

Figure 8:
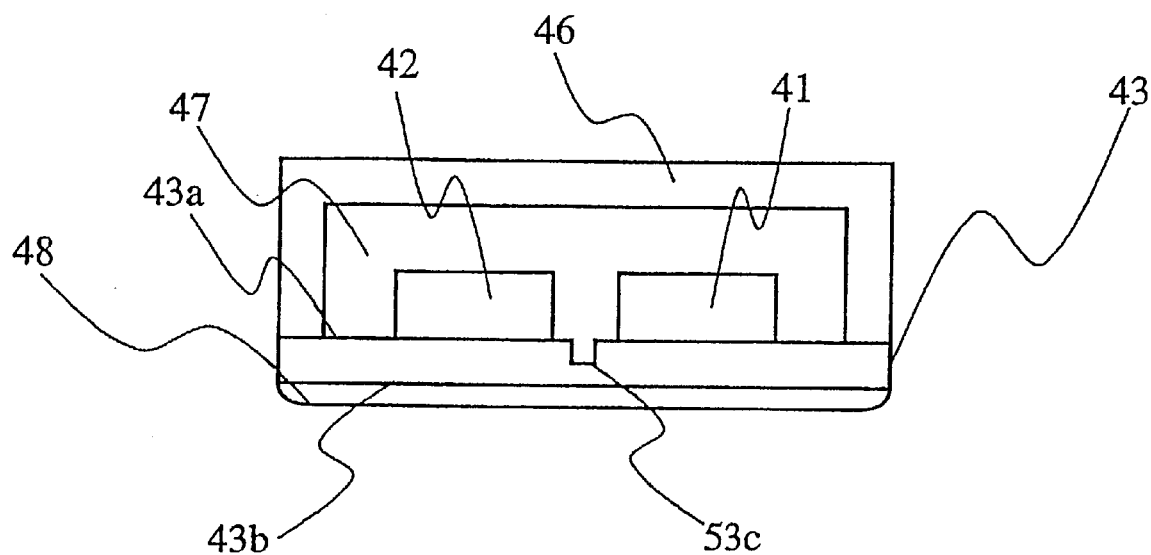
FIG. 8 is a main portion enlarged sectional view in which the sensor section of a 2nd embodiment of the ultrasonic diagnosis device of the present invention has been cut in the longitudinal direction of the belt, and is a drawing corresponding to FIG. 3 of the 1st embodiment.

FIG. 8 is a main portion enlarged sectional view in which the sensor section 4 has been cut in a longitudinal direction of the belt 50, and is a drawing corresponding to FIG. 3 of the aforesaid 1st embodiment.

As shown in FIG. 8, in the pulse wave detection device of this embodiment, in the substrate 43, a groove 53c is formed in a face at a piezoelectric elements 41, 42 side. This groove 53c is formed so as to extend between the transmitting piezoelectric element 41 and the receiving piezoelectric element 42. And, this groove 53c functions as an ultrasonic attenuation part for attenuating a propagation of the ultrasonic wave from the transmitting piezoelectric element 41 to the receiving piezoelectric element 42 through the substrate 43, thereby reducing a generation of noise owing to the ultrasonic wave propagated from the transmitting piezoelectric element. By further reducing the noise in this manner, it is possible to obtain a higher sensitivity.

Next, it is explained about a 3rd embodiment of the ultrasonic diagnosis device of the present invention. Incidentally, this 3rd embodiment is one in which the present invention has been applied also to the pulse wave detection device similarly to the aforesaid embodiments. In this 3rd embodiment, as to a member similar to the aforesaid 1st embodiment, the same reference numeral is affixed and its explanation is omitted.

Figure 9:
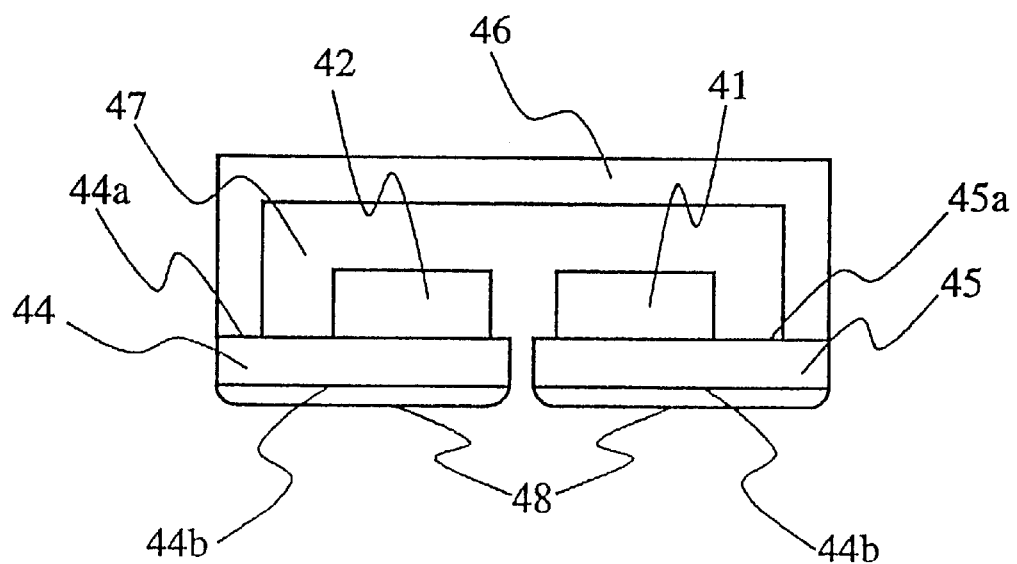
FIG. 9 is a main portion enlarged sectional view in which the sensor section of a 3rd embodiment of the ultrasonic diagnosis device of the present invention has been cut in the longitudinal direction of the belt, and is a drawing corresponding to FIG. 3 of the 1st embodiment.

FIG. 9 is a main portion enlarged sectional view in which the sensor section 4 has been cut in a longitudinal direction of the belt 50, and is a drawing corresponding to FIG. 3 of the aforesaid 1st embodiment.

As shown in FIG. 9, in the pulse wave detection device of this embodiment, a 1st substrate 44 having a transmitting piezoelectric element fixing part and a 2nd substrate 45 having a receiving piezoelectric element fixing part are formed respectively as mutually separate members, each of them is fixed to the support body 46 to form an approximately U-shaped form by the 1st substrate 44, the support body 46 and the 2nd substrate 45, and a gap is provided between the 1st substrate 44 and the 2nd substrate 45.

In this embodiment, the gap between the 1st substrate 44 and the 2nd substrate 45 becomes a flexible part, thereby exhibiting an effect similar to the aforesaid 2nd embodiment.

Incidentally, the present invention is not limited to the aforesaid embodiments, and various modifications are possible within a scope recited in each claim.

For example, in the aforesaid embodiments, as to the transmitting piezoelectric element 41 and the receiving piezoelectric element 42, the respective dimensions and the distance between them are set so as to be 0<b≧2d tan θ−c and satisfy c/(2d tan θ)≧0.1, but they may be set such that 2d tan θ−c <b<2d tan θ is satisfied and the receiving piezoelectric element 42 partially enters into the effective range W, and (2d tan θ−b)/(2d tan θ)≧0.1 is satisfied. Also in this case, among the reflected wave, 10% or more is received by the receiving piezoelectric element 42, so that it is possible to obtain an effect similar to the aforesaid embodiments.

Figure 10:
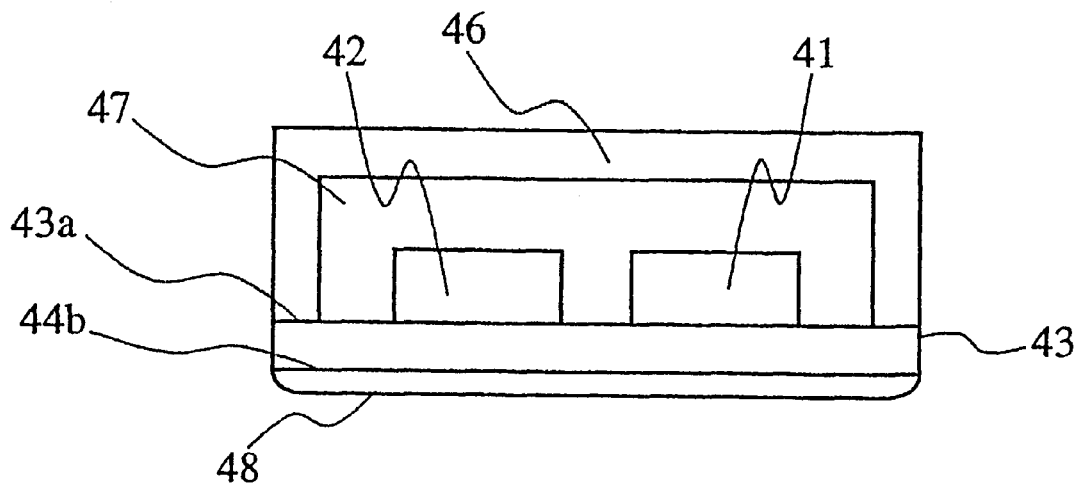
FIG. 10 is a main portion enlarged sectional view in which the sensor section of another example of the embodiment of the ultrasonic diagnosis device of the present invention has been cut in the longitudinal direction of the belt, and is a drawing corresponding to FIG. 3 of the 1st embodiment.

In each of the aforesaid embodiments, a space is provided between the substrate, the piezoelectric elements 41, 42 and the support body 46, and this space functions as an ultrasonic attenuation section. However, between the support body 46 and the piezoelectric elements 41, 42, there may be disposed a member for attenuating the ultrasonic wave or, as shown in FIG. 10, there may be formed an ultrasonic attenuation section 47 filled with a material for attenuating the ultrasonic wave such as an epoxy resin containing tungsten powders and a porous material consisting of a porous substance.

In each embodiment and each modified example, which have been mentioned above, the transmitting piezoelectric element 41 and the receiving piezoelectric element 42 are fixed to the substrate 43's face (one face) at a side opposite to the wearer, but they may be fixed to the other face becoming a wearer side. As such examples, modified examples in which the transmitting piezoelectric element 41 and the receiving piezoelectric element 42 have been fixed to the other face of the substrate 43 in the aforesaid 1st, 2nd and 3rd embodiments are shown respectively in FIG. 11, FIG. 12 and FIG. 13. Incidentally, in the modified example of FIG. 12, the groove 53c is formed also in a side of the other face of the substrate with the fact that the transmitting piezoelectric element 41 and the receiving piezoelectric element 42 have been fixed to the other face. And, by this groove 53c, the propagation of the ultrasonic wave from the transmitting piezoelectric element 41 to the receiving piezoelectric element 42 is attenuated through the substrate 43, so that the generation of noise owing to the ultrasonic wave propagated from the transmitting piezoelectric element is reduced and thus it is possible to obtain the high sensitivity. Incidentally, from a point of attenuation efficiency of the ultrasonic wave, it is preferable that this groove 53c is formed in the face at a side to which the piezoelectric elements 41, 42 are fixed.

Figure 11:
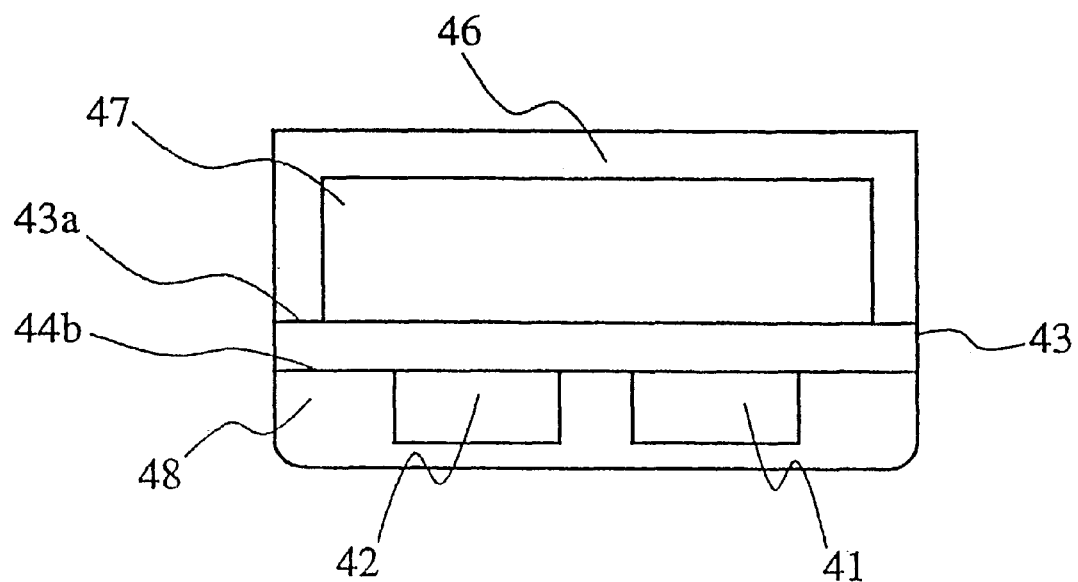
FIG. 11 is a main portion enlarged sectional view in which the sensor section of another example of the embodiment of the ultrasonic diagnosis device of the present invention has been cut in the longitudinal direction of the belt, and is a drawing corresponding to FIG. 3 of the 1st embodiment.
Figure 12:
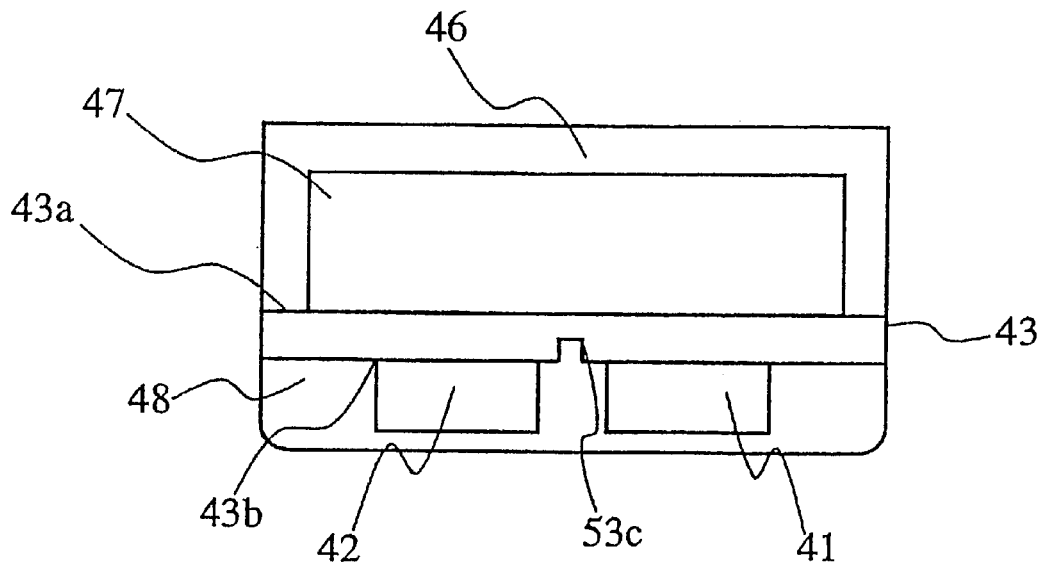
FIG. 12 is a main portion enlarged sectional view in which the sensor section of another example of the embodiment of the ultrasonic diagnosis device of the present invention has been cut in the longitudinal direction of the belt, and is a drawing corresponding to FIG. 3 of the 1st embodiment.
Figure 13:
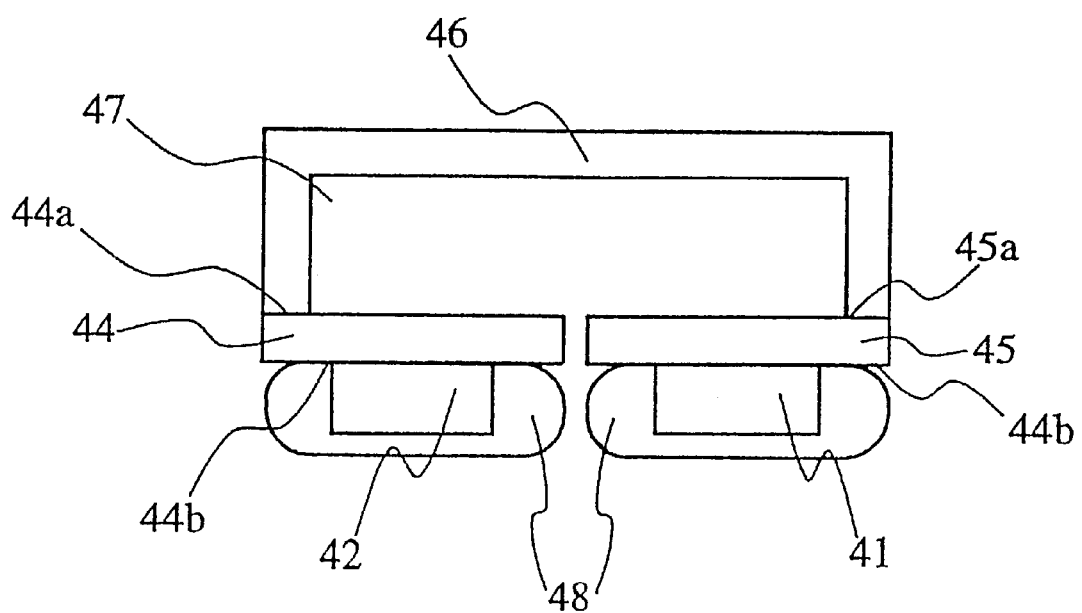
FIG. 13 is a main portion enlarged sectional view in which the sensor section of another example of the embodiment of the ultrasonic diagnosis device of the present invention has been cut in the longitudinal direction of the belt, and is a drawing corresponding to FIG. 3 of the 1st embodiment.
Figure 14:
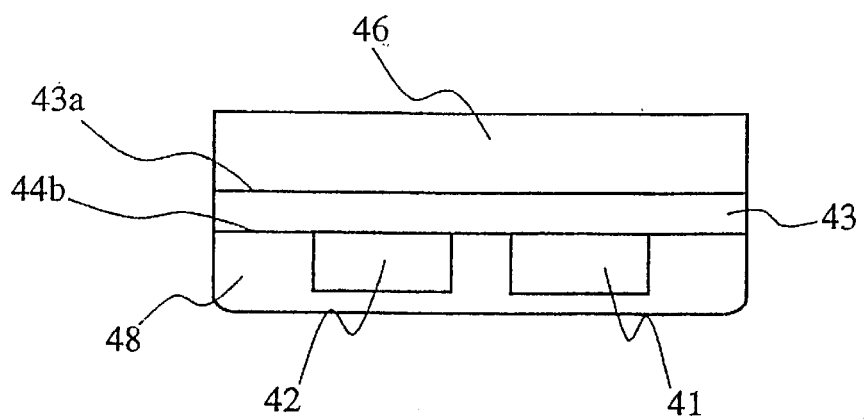
FIG. 14 is a main portion enlarged sectional view in which the sensor section of another example of the embodiment of the ultrasonic diagnosis device of the present invention has been cut in the longitudinal direction of the belt, and is a drawing corresponding to FIG. 3 of the 1st embodiment.
Figure 15:
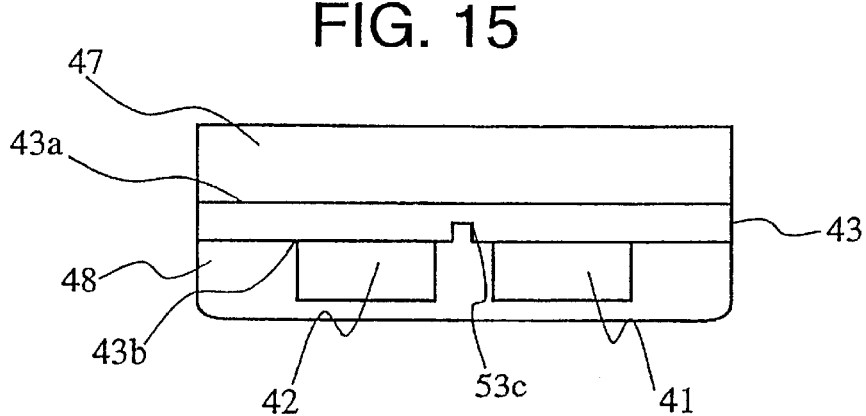
FIG. 15 is a main portion enlarged sectional view in which the sensor section of another example of the embodiment of the ultrasonic diagnosis device of the present invention has been cut in the longitudinal direction of the belt, and is a drawing corresponding to FIG. 3 of the 1st embodiment.
Figure 16:
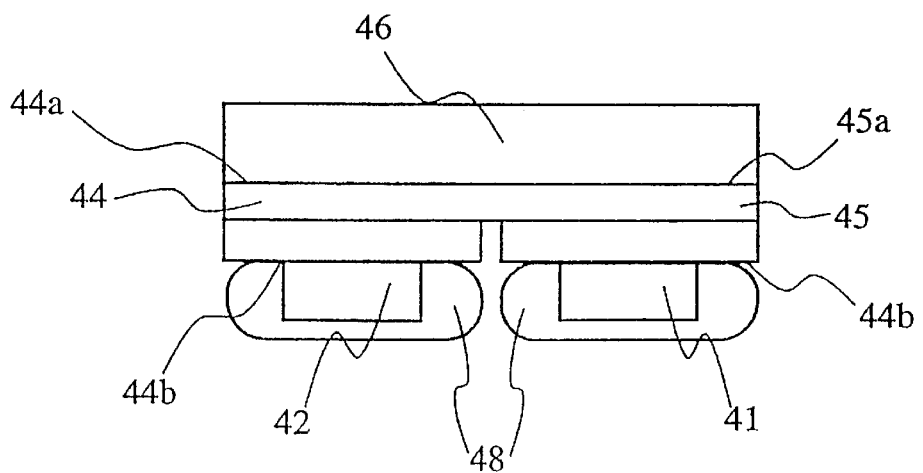
FIG. 16 is a main portion enlarged sectional view in which the sensor section of another example of the embodiment of the ultrasonic diagnosis device of the present invention has been cut in the longitudinal direction of the belt, and is a drawing corresponding to FIG. 3 of the 1st embodiment.
Figure 17:
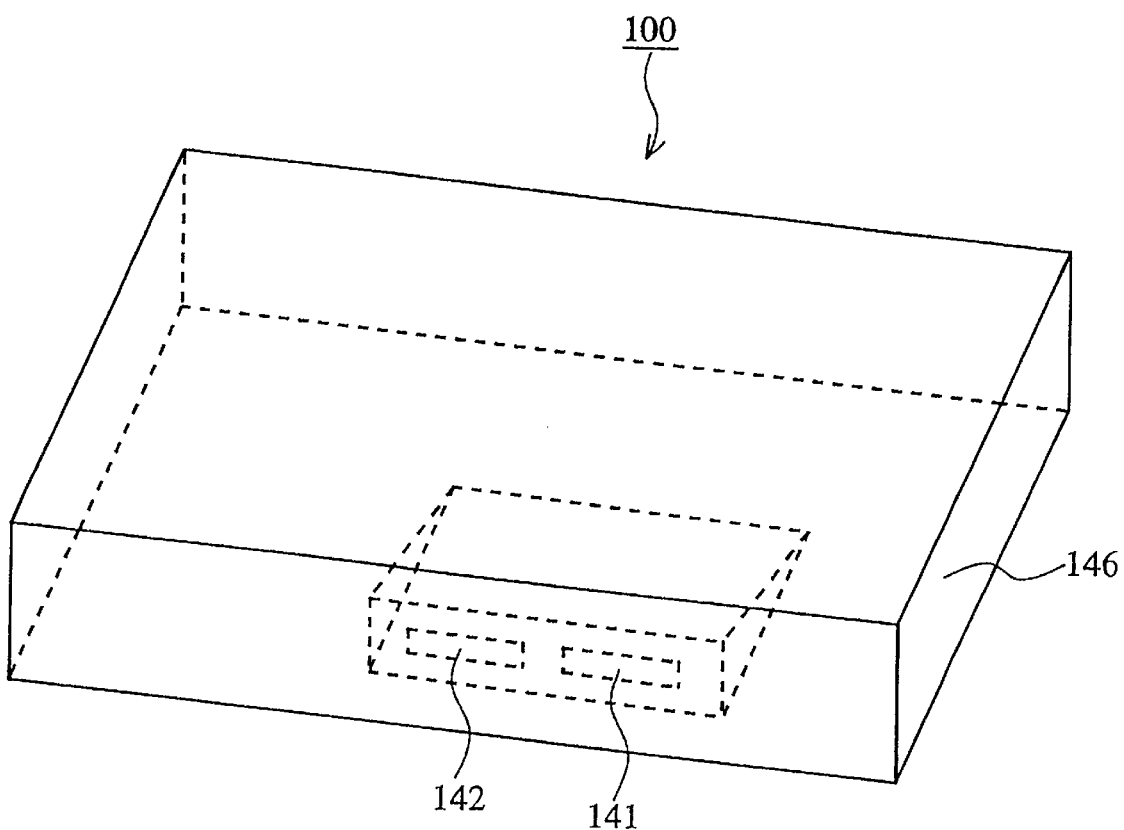
FIG. 17 is a perspective view showing a sensor section of an ultrasonic diagnosis device of the prior art.

In each embodiment and each modified example, which have been mentioned above, the support body 46 is formed in the approximately U-shaped form in section so as to become a box form whose top face is opened to thereby provide the space accommodating the piezoelectric elements 41, 42 and functioning as the ultrasonic wave attenuation section, but the shape having the space is not limited to this, and a shape whose top face and side face have been opened may be adopted. Besides, as shown in FIG. 11 to FIG. 13, in case where the piezoelectric elements 41, 42 are fixed to the other face, since the support body 46 is unnecessary to accommodate these piezoelectric elements 41, 42, there may be adopted a shape in which it is brought in its whole face into contact with the other face of the substrate 43. As such examples, in FIG. 14 to FIG. 16, there are shown examples in each of which the support body 46 has been made into a plate form and secured to the other face of the substrate 43.

The flexible part provided in the substrate 43 is not limited to one provided by the shape such as forming the groove 53c and the gap in the substrate 43, and it may be adapted such that a portion among the substrate 43 between the transmitting piezoelectric element fixing part and the receiving piezoelectric element fixing part is constituted by a separate member having a flexibility.

In each embodiment and each modified example, which have been mentioned above, the ultrasonic diagnosis device is the pulse wave detection device, but the ultrasonic diagnosis device to which the present invention is applied is not limited to the pulse wave detection device. The ultrasonic diagnosis device of the present invention may be one comprising a transmitting piezoelectric element for transmitting an ultrasonic wave to a diagnosis region, a receiving piezoelectric element for receiving a reflected wave of the ultrasonic wave from the diagnosis region, support means for supporting the transmitting piezoelectric element and the receiving piezoelectric element, and information obtainment means for obtaining an information of the diagnosis region on the basis of the reflected wave received by the receiving piezoelectric element, and, for example, it may be an image diagnosis device for obtaining an image inside a body by the ultrasonic wave, an ultrasonic flaw detection device for searching flaws in a building or the like by the ultrasonic wave, various measuring devices or the like. Besides, by applying the present invention to a sensor device comprising a transmitting piezoelectric element for transmitting an ultrasonic wave to a diagnosis region, a receiving piezoelectric element for receiving a reflected wave of the ultrasonic wave from the diagnosis region, and a support means for supporting the transmitting piezoelectric element and the receiving piezoelectric element, which are used in such an ultrasonic diagnosis device, it is possible to obtain similar actions and effects.

Each modified example mentioned above can be adopted by being suitably overlapped.

As explained above, according to the ultrasonic diagnosis device of the present invention, the simple manufacture is possible, and it is possible to obtain high sensitivity and measuring accuracy.

What is claimed is:

1. An ultrasonic diagnosis device comprising:

a transmitting piezoelectric element for transmitting an ultrasonic wave to a diagnosis region, a receiving piezoelectric element for receiving a reflected wave of the ultrasonic wave from the diagnosis region, support means for supporting the transmitting piezoelectric element and the receiving piezoelectric element, and information obtainment means for obtaining an information of the diagnosis region on the basis of the reflected wave received by the receiving piezoelectric element, wherein the support means has a planar face disposed approximately parallel to the diagnosis region, and the transmitting piezoelectric element and the receiving piezoelectric element are disposed on the planar face of the support means by a relation satisfying the following conditions 1 or conditions 2 in case where it is supposed that a width of the transmitting piezoelectric element is a, a distance between the transmitting piezoelectric element and the receiving piezoelectric element b, a width of the receiving piezoelectric element c, a distance up to a measuring region d and a directivity angle θ:

$$c/(2d \tan \theta) \geq 0.1 \text{ and } 0 < b \geq 2d \tan \theta - c \quad \text{conditions 1}$$

$$(2d \tan \theta - b)/(2d \tan \theta) \geq 0.1 \text{ and } 2d \tan \theta - c < b < 2d \tan \theta. \quad \text{conditions 2}$$

2. An ultrasonic diagnosis device comprising:

a transmitting piezoelectric element for transmitting an ultrasonic wave to a diagnosis region, a receiving piezoelectric element for receiving a reflected wave of the ultrasonic wave from the diagnosis region, support means for supporting the transmitting piezoelectric element and the receiving piezoelectric element, and information obtainment means for obtaining an information of the diagnosis region on the basis of the reflected wave received by the receiving piezoelectric element, wherein the support means has a planar face disposed parallel to the diagnosis region, and the transmitting piezoelectric element and the receiving piezoelectric element are disposed on the planar face of the support means such that their widths are respectively 0.38 to 1.1 mm, and a gap between them is 0.05 to 4.0 mm.

* * * * *